(12) United States Patent
Gokaraju et al.

(10) Patent No.: US 11,147,850 B2
(45) Date of Patent: Oct. 19, 2021

(54) SYNERGISTIC COMPOSITION FOR OSTEOARTHRITIS

(71) Applicant: LAILA NUTRACEUTICALS, Vijayawada (IN)

(72) Inventors: Ganga Raju Gokaraju, Vijayawada (IN); Rama Raju Gokaraju, Vijayawada (IN); Venkata Kanaka Ranga Raju Gokaraju, Vijayawada (IN); Trimurtulu Golakoti, Vijayawada (IN); Kiran Bhupathiraju, Vijayawada (IN)

(73) Assignee: Laila Nutraceuticals, Vijayawada Andhra Pradesh (IN)

( * ) Notice: Subject to any disclaimer, the term of this patent is extended or adjusted under 35 U.S.C. 154(b) by 808 days.

(21) Appl. No.: 15/518,107

(22) PCT Filed: Oct. 9, 2015

(86) PCT No.: PCT/IN2015/000382
§ 371 (c)(1),
(2) Date: Apr. 10, 2017

(87) PCT Pub. No.: WO2016/156026
PCT Pub. Date: Apr. 14, 2016

(65) Prior Publication Data
US 2017/0290875 A1 Oct. 12, 2017

(30) Foreign Application Priority Data
Oct. 10, 2014 (IN) .......................... 5106/CHE/2014

(51) Int. Cl.
| | |
|---|---|
| *A61K 36/9066* | (2006.01) |
| *A61K 36/48* | (2006.01) |
| *A61K 9/00* | (2006.01) |
| *A61K 31/353* | (2006.01) |
| *A61K 31/715* | (2006.01) |

(52) U.S. Cl.
CPC ........ *A61K 36/9066* (2013.01); *A61K 9/0014* (2013.01); *A61K 9/0053* (2013.01); *A61K 31/353* (2013.01); *A61K 31/715* (2013.01); *A61K 36/48* (2013.01); *A61K 2236/33* (2013.01)

(58) Field of Classification Search
None
See application file for complete search history.

(56) References Cited

U.S. PATENT DOCUMENTS

| | | | |
|---|---|---|---|
| 2008/0286387 A1 | 11/2008 | Majeed et al. | |
| 2012/0021077 A1* | 1/2012 | Patwardhan ........... | A61K 36/81 424/756 |

OTHER PUBLICATIONS

Ushanandini, et al., Phytotherapy Research, 20:851. (Year: 2006).*
Vyas, et al., International Journal of PharmTech Research, 2:1543. (Year: 2010).*
Funk, et al., J. Nat. Prod., 69:351. (Year: 2006).*
Babaria, et al., International Journal of Pharmacy and Pharmaceutical Scienes, 3:204. (Year: 2011).*
Ammon, et al., "Pharmacology of Curcuma longa", Planta Med. 57(1991) 1-7.
Chung, et al., "Lipoxygenase inhibiting activity of some Malaysian plants", Pharmaceutical Biology, 2009; 47(12): 1142-1148.
Knight, et al., "Protease-activated receptors in human airways: Upregulation of PAR-2 in respiratory epithelium from patients with asthma", J. Allergy Clin. Immunol., vol. 108, No. 5: 797-803.
Weiss, et al., "Osteoarthritis Revisited: A Contemporary Review of Aetiology", International Journal of Osteoarchaeology; Int. J. Osteoarchaeol. (in press) Published online in Wiley InterScience; (www.interscience.wiley.com) DOI: 10.1002/oa.889; 2007, 17:437-450.

* cited by examiner

*Primary Examiner* — Michael Barker
(74) *Attorney, Agent, or Firm* — Kramer Amada

(57) ABSTRACT

The present invention relates to synergistic compositions for the treatment of one or more associated conditions of arthritis or rheumatoid arthritis osteoarthritis. More particularly, novel synergistic compositions which comprises a combination of therapeutically effective amounts of: a) an alcoholic/hydroalcoholic extract of *Tamarindus indica* seed comprising proanthocyanidins either alone or in combination with water extract of *Tamarindus indica* seed comprising polysaccharides, b) a *Curcuma longa* rhizome extract comprising curcuminoids, c) optionally containing pharmaceutically or nutraceutically or dietetically acceptable carriers/excipients. The invention also relates to a method of treating one or more associated conditions of arthritis or rheumatoid arthritis or osteoarthritis using synergistic composition.

14 Claims, 2 Drawing Sheets

Catechin

Epi-catechin

| S.No | Unit number | Name |
|---|---|---|
| 1 | n = 0 | Procyanidin B2 (dimer) |
| 2 | n = 1 | Procyanidin C1 (trimer) |
| 3 | n = 2 | Procyanidin tetramer |
| 4 | n = 3 | Procyanidin pentamer |
| 5 | n = 4 | Procyanidin hexamer |

SYNERGISTIC COMPOSITION FOR OSTEOARTHRITIS

FIELD OF THE INVENTION

The present invention relates to synergistic compositions for the treatment of one or more associated conditions of arthritis or rheumatoid arthritis or osteoarthritis. More particularly, the invention relates to a synergistic composition comprising a combination of therapeutically effective amounts of *Tamarindus indica* seed extracts and *Curcuma longa* rhizome extracts, optionally in association with an excipient/carrier/diluent.

BACKGROUND OF THE INVENTION

Osteoarthritis (OA) is a joint degeneration disease and it affects more people than any other joint diseases due to the pain and dysfunction it causes. Osteoarthritis is one of the most widespread forms of degenerative joint and bone diseases. According to Center for Disease Control, USA, OA affects 13.9% of adults aged 25 and older and 33.6% (12.4 million) of those 65 and over. The pathological condition is characterized by localized areas of loss of articular cartilage within the synovial joints, associated with hypertrophy of the bone and thickening of the joint capsule. The cause of osteoarthritis is thought to involve a complex interaction of cells and soluble mediators such as cytokines, growth factors, inflammatory mediators, metalloproteinases, and chondrodegradative enzymes. This complex interaction may further be triggered by physical trauma, surgery, infection, or other disease process. In its more advanced stages, osteoarthritis is characterized by fraying and fibrillation of cartilage resulting from the elaboration of proteolytic and collagenolytic enzymes by the chondrocytes that initially attack the joint matrix.

The disease progression may range from relatively mild symptoms causing pain and swelling to extreme debilitation and physical incapacitation. Complete destruction of the cushioning tissue in the joints may also leads to bone erosion. The high prevalence of this disease not only affects the individuals who suffer from it, but also presents increasing costs to the health-care industry and loss of productivity in the workplace. About 35-50% of OA cases may be genetically determined. Other risk factors include excess body mass, joint injury, excessive mechanical stress, malalignment, female gender, and ageing (Int. J. Osteoarchaeology, 2007, 17:437-450). The intertwined abnormalities of cartilage, bone and synovium lead to joint degeneration.

Treatment regimens for osteoarthritis include pharmaceutical treatments that directly mediate the cellular/inflammatory cytokine interaction and perpetuate the progression of the disease. While over-the-counter medications and prescription drugs are provided for symptomatic relief they cause a number of side effects. For example, long-term use of high dosage non-steroidal anti-inflammatory drugs such as aspirin, ibuprofen or acetaminophen may lead to upset stomachs, gastrointestinal bleeding and possible liver damage. Stronger prescription drugs such as corticosteroids may lead to brittle bones, cataracts and elevated blood sugar.

*Tamarindus indica* L. Common Name: Indian Tamarind, Tamarind

Tamarind (*Tamarindus indica*) is a monotypic species, meaning that there is only one species within the genus *Tamarindus*. This tropical plant mainly originated from native Africa and spread throughout the African continent. It grows wild in Sudan and in India. Tamarind (*Tamarindus indica* L.) is an evergreen tree, slow growing but long living plant, which can measure between 15 and 25 meters in height and up to7.5 meters in circumference. It has deep roots, rough dark gray bark and strong branches, flexible to withstand the high winds. The tamarind trees start producing fruits at the age between 3 and 7 years. It reproduces by seed. Berry production stabilizes at the age of 15. The tree is productive up to 40 to 60 years. Tamarind seeds are hard, brown and wrapped in protective endocarp layer. A sheath generally contains between 2 and 10 seeds, each 1 cm in diameter. Commonly used parts of *T. indica* are flowers, pulp of fruit, seeds, leaves, root, trunk or bark.

US patent application US 2008/0286387 disclosed extraction process of *Tamarindus indica* seed coat.

Turmeric, the powdered rhizome of the herb *Curcuma longa* L. (Zingiberaceae) is used extensively in Indian and Asian cuisine and it is also used as a coloring and flavoring agent. Powdered turmeric, or its extract, is found in numerous commercially available botanical supplements. In Ayurvedic medicine, turmeric has traditionally been used to treat inflammation, skin wounds and tumors (Ammon and Wahl, 1991, Planta Med., 57:1-7). Curcuminoids are the major active compounds found in *Curcuma longa*. Turmeric extracts and Curcuminoids have been reported to have anti-microbial, anti-inflammatory, antioxidant and anticancer effects. Alcohol extract of *C. longa* comprising total curcuminoids is used for demonstrating the current invention. Other solvent extracts or fractions enriched in total curcuminoids can also be used.

There is however no prior art, to the best of inventor's knowledge, relating to the compositions comprising extracts derived from *Tamarindus indica* seed and *Curcuma longa* rhizome for enriching anti-arthritis activity.

Therefore, the main object of the present invention is to provide synergistic nutraceutical or dietary supplement compositions comprising therapeutically effective combination of extracts or fractions from *Tamarindus indica* and *Curcuma longa*.

SUMMARY OF THE INVENTION

To remedy the aforementioned shortcomings, the present invention discloses a novel synergistic composition which comprises a combination of therapeutically effective amounts of:
a) An alcoholic/hydro alcoholic extract of *Tamarindus indica* seed comprising proanthocyanidins either alone or in combination with water extract of *Tamarindus indica* seed comprising polysaccharides,
b) A *Curcuma longa* rhizome extract comprising curcuminoids,
c) Optionally containing pharmaceutically or nutraceutically or dietetically acceptable carriers/excipients useful for the prevention or treatment of at least one condition selected from inflammation, arthritis, joint pain, rheumatoid arthritis, osteoarthritis, chronic non-rheumatoid arthritis, collagen degradation.

In an aspect, the alcohol used for preparing *Tamarindus indica* seed extract comprising proanthocyanidin compounds selected from the group consisting of methanol, ethanol, propanol, isopropanol, butanol and tert-butanol and mixtures thereof. The *Curcuma longa* extract may be prepared from *Curcuma longa* rhizome using solvents selected from the group consisting of methanol, ethanol, propanol, isopropanol, n-butanol, tert-butanol, acetone, ethyl acetate and the fractions enriched in total curcuminoids derived from the said extracts.

The pharmaceutically or nutraceutically or dietetically acceptable carriers/excipients that can be used for formulating the inventive compositions may be selected from surfactants, binders, diluents, disintegrants, lubricants, preservatives, stabilizers, buffers, polymers, colors, flavors, suspensions and drug delivery systems.

In a preferred aspect, the synergistic composition(s) of the invention comprises (a) *Tamarindus indica* seed extract varies in the range from 20% to 80%, (b) *Curcuma longa* rhizome extract varies in the range of 20% to 60%; and (c) optionally containing excipients/carriers varying in the range of 0-30%.

In an alternate aspect, the invention provides a novel synergistic *Tamarindus indica* seed extract comprising a) 1% to 99% by weight of alcohol or hydroalcohol extract primarily consisting of proanthocyanidins and b) 1 to 50% by weight of water extract consisting of predominantly polysaccharides, optionally containing pharmaceutically or nutraceutically or dietetically acceptable carriers/excipients useful for the treatment of at least one disease condition selected from inflammation, arthritis, joint pain, rheumatoid arthritis and osteoarthritis.

In yet another aspect, the present invention provides a method for preventing or treating at least one condition selected from inflammation, arthritis, joint pain, rheumatoid arthritis, osteoarthritis, chronic non-rheumatoid arthritis, collagen degradation in a patient which method comprises administering to the patient an effective amount of synergistic composition comprising a) an alcoholic/hydroalcoholic extract of *Tamarindus indica* seed comprising proanthocyanidins either alone or in combination with water extract of *Tamarindus indica* seed comprising polysaccharides; b) *Curcuma longa* rhizome extract comprising curcuminoids, optionally containing pharmaceutically or nutraceutically or dietetically acceptable carriers/excipients, to the patient in need thereof.

In a further aspect, the invention provides a method for treating a disease condition selected from inflammation, arthritis, joint pain, rheumatoid arthritis, osteoarthritis, chronic non-rheumatoid arthritis, collagen degradation in a patient in need thereof comprising administering to the patient an effective amount of novel synergistic *Tamarindus indica* seed extract comprising a) 1% to 99% by weight of alcohol or hydroalcohol extract primarily consisting of proanthocyanidins and b) 1 to 50% by weight of water extract consisting of predominantly polysaccharides, optionally containing pharmaceutically or nutraceutically or dietetically acceptable carriers/excipients.

The novel synergistic composition(s) according to present invention may be formulated to be administered orally or topically. Accordingly, the pharmaceutical/Nutraceutical composition may be prepared in a form of a tablet, soft gel, capsule, granule, powder, liquid, solution, cream, lotion, spray, implant, or transdermal patch for various administration routes.

In yet another aspect, the invention provides use of a novel synergistic composition comprising a combination of therapeutically effective amount of; a) A *Tamarindus indica* seed extract selected from alcohol or hydroalcohol extract comprising proanthocyanidins either alone or in combination with *Tamarindus indica* seed water extract containing polysaccharides, b) a *Curcuma longa* rhizome extract comprising curcuminoids, c) optionally containing pharmaceutically or Nutraceutically or dietetically acceptable carriers/ excipients for the prevention or treatment of at least one condition selected from inflammation, arthritis, joint pain, rheumatoid arthritis, osteoarthritis, chronic non-rheumatoid arthritis, collagen degradation.

The details of one or more embodiments of the invention are set forth in the description below. Other features or advantages of the present invention will be apparent from the following detailed description of several embodiments, and also from the appended claims.

DETAILED DESCRIPTION OF THE INVENTION

Unless otherwise defined, all technical and scientific terms used herein have the same meaning as commonly understood by one of ordinary skill in the art to which this invention pertains.

Inflammation is a response of the vascular tissues to stimuli such as pathogens, damaged cells or allergic agents, which enter into the body. It is a protective mechanism by the organism to remove harmful pathogens or agents and protect the tissues. Pro-inflammatory cytokines such as TNFα, IL-β, IL-6, GM-CSF and CD4+, Th2 subset derived IL-4, IL-5 and IL-13 lymphokines are considered as the key factors of immunopathogenesis of inflammatory diseases [Knight D A, et. al., J. Allergy Clin. Immuno1.2001; 108: 797-803].

5-Lipoxygenase is an enzyme critical for leukotriene synthesis from arachidonic acid, a key step in the inflammatory process. Leukotrienes are key mediators of inflammatory disease. The activation and gene expression of 5-lipoxygenase (5-LOX) is responsible for the inflammatory disease condition. Hence blocking or down regulating the 5-LOX is an effective therapeutic approach for the treatment and control of inflammatory condition.

Tumor necrosis factor-alpha (TNFα) is an important pleiotropic pro-inflammatory cytokine produced predominantly by macrophages. TNF-α is an acute phase protein and chemotaxin, which initiates a cascade of cytokines and increases vascular permeability, thereby recruiting macrophage and neutrophils to the site of infection. High levels of TNFα, however, will have detrimental effects and lead to many disease conditions. Hence, TNFα is an important target for developing novel treatments against a wide range of inflammatory diseases.

Matrix Metalloproteinases (MMPs) are zinc dependent endopeptidases, that are capable of breaking down all kinds of extra cellular matrix proteins, such as collagen, and proteoglycan, and can cause diseases of the cartilages and inflammation. MMPs are divided primarily into three principal groups, the fibroblast collagenase-1 (MMP-1), the gelatinases comprising gelatinase A (MMP-2) and the gelatinase B (MMP-9), and the stromelysines comprising stromelysine-1 (MMP-3). The expression of MMP-3 protein is closely related to pathogenic mechanism of OA. Hence, it may be an important indicator of early diagnosis and treatment of osteoarthritis.

Figure 1:
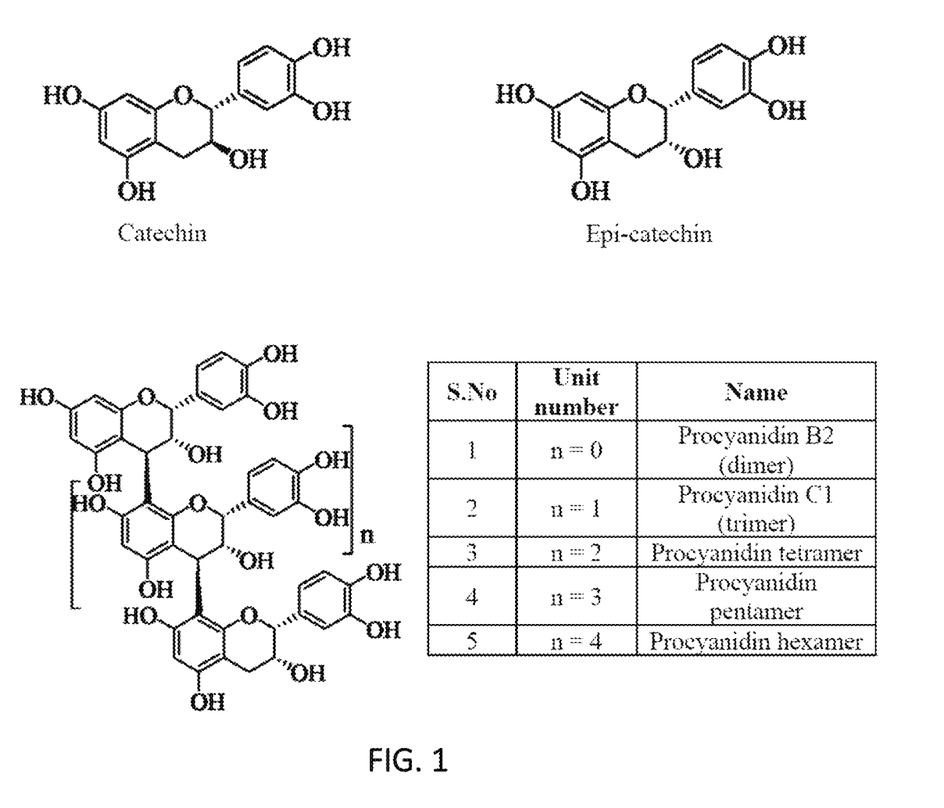
FIG. 1 represent various Flavanols and proanthocyanidin compounds isolated and characterized from methanol extract of *T. indica* seed (Extract-1).

During the search for novel compounds having anti-inflammatory and anti-osteoarthritis activities, the inventors found that the alcohol extracts of *Tamarindus indica* seed have some unexpected properties. The extracts of *T. indica* powdered seed raw material produced using methanol (Extract-1) or ethanol (Extract-1A) as medium of extraction contains predominantly proanthocyanidins (PAC), when analyzed as per the Spectrophotometric method (USP 29-NF 24 page 2552). Purification of the extract by extensive chromatography on flash and preparative HPLC systems, followed by NMR and LC-MS/MS analysis on waterXevoG2QTOF mass spectrometer showed the presence of catechin, epicatechin, procyanidinB2 (diamer), procyanidinC1 (trimer), procyanidin (tetramer), procyanidin (pentamer) and procyanidin (hexamer) as summarized in (FIG. 1). Extraction with aqueous alcohol or other organic solvents selected from acetone, propanol, isopropanol, butanol, tert-butanol and mixtures thereof or their aqueous solution with small percentage of water also yielded proanthocyanidin containing extracts. The water extract of *T. indica* seed (Extract-4) on the other hand possesses predominantly polysaccharide compounds with negligible quantity of proanthocyanidin compounds. The *Tamarindus* Seed extract or fraction containing *Tamarindus* Seed Polysaccharide (TSP) has unique properties. Similarly, the methanol or ethanol extract of *T. indica* seeds that contain proanthocyanidin (PAC) compounds also exhibit unique properties and they are different from TSP containing extract or fraction as illustrated in the following table (Table 1).

TABLE 1

Comparison of properties for alcohol and water extracts of *T. indica*

| SNO | TEST | Water Extract of *T. indica* (Extract-4) | Methanol extract of *T. indica* (Extract-1) |
|---|---|---|---|
| 1 | WSE | 78.34% | 84.29% |
| 2 | ASE | 5.47% | 99.00% |
| 3 | $p^H$ | 6.65 | 5.09 |
| 4 | Polysaccharides | 24.49% | NIL |
| 5 | Proanthocyanidins | 0.36% | >90% |

WSE is water soluble extractives;
ASE is alcohol extractives

The *Tamarindus indica* seed extract/fraction used in the current invention can be an extract derived from *Tamarindus indica* seed using alcohol or hydroalcohol or a mixed extract containing alcohol extract and water extract of *Tamarindus* seed. In a unique process, the *T. indica* seed extract used in the present invention can be obtained by powdering *T. indica* seeds and then extracting the powder with an alcohol such as methanol or ethanol to obtain Extract-1 or Extract-1A respectively. The left over seed residue after alcohol extraction was then extracted with water to obtain *Tamarindus* seed residue water extracts (Extract-2/Extract-2A). Alternately, extraction of seed powder directly with water yielded Extract-4. The alcoholic extracts of *T. indica* seed showed very potent 5-lipoxygenase (5-LOX) and cyclooxygenase (COX) inhibition activities, and they also showed potent inhibition of TNFα and MMP-3 as summarized in tables-3, -4 and -5. The water extracts (Extract-2/Extract-2A/Extract-4) of *T. indica* seed in comparison showed inferior efficacy in the above studies. The concentrated alcoholic and water extracts were combined at desired ratio to obtain the new extracts (Extracts-3, -5, -6 and -7). Alternatively, the extract solutions were combined and evaporated to obtain mixed new extracts. Extract-3 and Extract-5 are obtained by combining the alcohol extract (Extract-1) and water extract (Extract-2) in 1:1 and 10:1 ratios respectively. Different extracts prepared as part of the invention are summarized in Table 2. It was found surprisingly that mixed extracts (Extract-3, Extract-5, Extract-6 and Extract-7) of *T. indica* obtained by combining its proanthocyanidin containing alcohol extracts (Extract-1 or Extract-1A) or their fractions with Tamarind seed polysaccharide containing water extract (Extract-2 or Extract-4) or their fraction showed unique/improved biological properties. The mixed extracts, Extract-3, Extract-5 and Extract-6 for example showed percentage MMP-3 inhibitions of 46.71%, 39.58% and 46.52% respectively in human SW982 synovial cells at 25 µg/ml concentration, when compared to 26.02% (Extract-1), 0% (Extract-2) and 0% (Extract-4) inhibitions exhibited by their individual extracts as summarized in Table-5. Similarly, the mixed extracts, Extract-3, Extract-5, Extract-6 and Extract-7 showed more potent 5-lipoxygenase inhibitory activity with half maximal inhibitory concentrations (IC50s) of 12.02, 13.05, 10.72 and 11.08 µg/mL respectively, when compared to 15.62 µg/mL, >100 µg/mL and >100 µg/mL for IC50s exhibited by individual extracts, Extract-1, Extract-2 and Extract-4 respectively as summarized in Table-3. This manifests that the extracts or fraction of *T. indica* containing proanthocyanidins work in synergism with the extracts or fractions containing polysaccharides.

TABLE 2

Description of Extracts

| S. No | Test substance | Description |
|---|---|---|
| 1 | Extract-1 | *Tamarindus indica* seed methanol extract |
| 2 | Extract-2 | *Tamarindus indica* seed residue (left over after methanol extraction) water Extract |
| 3 | Extract-3 | Blend of Extract-1 and Extract-2 in the ratio 1:1 |
| 4 | Extract-4 | *Tamarindus indica* water Extract (Direct water extract) |
| 5 | Extract-5 | Blend of Extract-1 and Extract-2 in the ratio 10:1) |
| 6 | Extract-6 | Blend of Extract-1 and Extract-4 in the ratio 10:1 |
| 7 | Extract-7 | Blend of Extract-1 and Extract-2 in the ratio 5:1) |
| 8 | Extract-8 | *Curcuma longa* alcohol Extract |

Figure 2A:
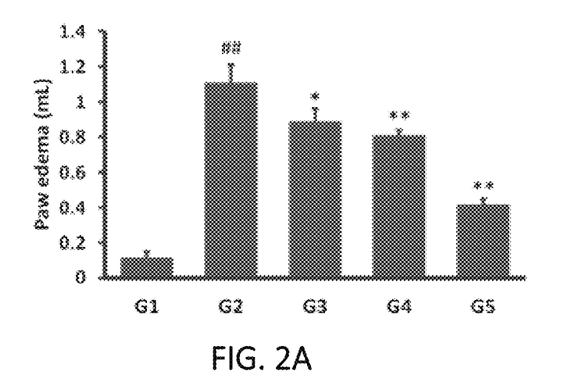
FIGS. 2A to 2C are bar diagrammatic representations of rat paw edema (FIG. 2A), percent inhibition of paw edema (FIG. 2B) and percent weight bearing (FIG. 2C). Each bar represents mean±S.E.M, n=6. $^{\#\#}p<0.01$ vs normal control (G1); $*p<0.05$; $**p<0.01$ vs AIA control (G2) by One-way ANOVA followed by Dunnett's Test. G3 and G4 are treatment groups supplemented with 200 and 400 mg/kg body weight of composition-11 and G5 is treatment group supplemented with 10 mg/kg body weight of prednisolone.
Figure 2B:
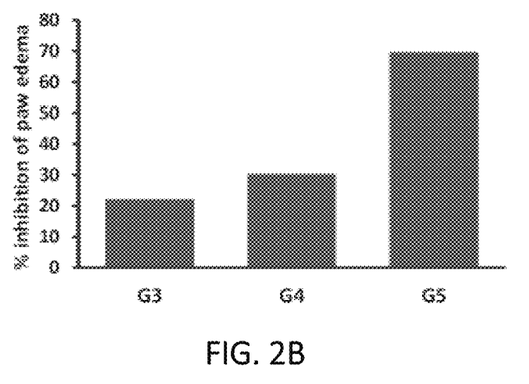
Figure 2C:
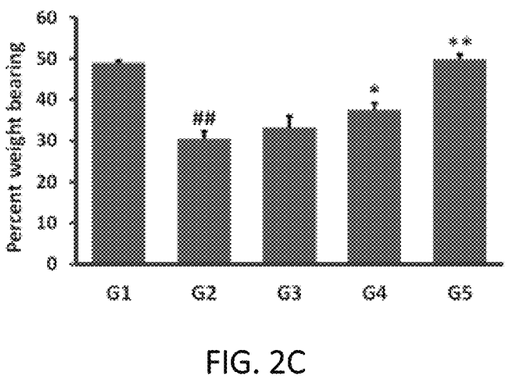

It was also found surprisingly that the compositions containing *Tamarindus indica* seed extracts shows synergism when combined with *Curcuma longa* extracts. Alcohol extract of *C. longa* comprising total curcuminoids is used for demonstrating the current invention. Other solvent extracts or fractions enriched in total curcuminoids can also be used. For example, composition-1 and Composition-2 containing the *T. indica* methanol extract (Extract-1) and *Curcuma longa* methanol extract (Extract-8) in 1:1 and 2:1 respectively showed half maximal inhibitory concentrations (IC50s) of 8.98 and 7.81 µg/mL respectively, when compared to those of the individual ingredients, Extract-1 (15.62 µg/mL) and Extract-8 (17.96 µg/mL) (Table 3). Hence, the efficacy shown by the compositions are better than the corresponding individual ingredients suggesting synergistic inhibition of 5-Lipoxygenase enzyme by the extracts of *T. indica* and *C. longa*. Similarly, other compositions (Compositions-3 to -7) also showed inhibitions, which were found to be better than the additive effect contributed by the corresponding individual ingredients as summarized in table 3. In addition, the *Tamarindus indica* seed extracts also showed synergistic inhibition of the cytokine TNFα when combined with *Curcuma longa* rhizome extracts. The compositions-1 to -10 showed superior inhibition of TNFα which is better than the inhibition exhibited by the corresponding individual ingredients at the similar dose and/or better than the additive effect estimated for the individual ingredients. For, example the compositions-1, -2, -3 and -4 exhibited 99.2, 81.94, 65.09 and 95.25% inhibition of TNFα respectively at 10 μg/ml concentration, when compared to the 48.13% and 78.78% inhibition respectively exhibited by the corresponding individual ingredients, *Tamarindus indica* seed methanol extract (Extract-1) and *Curcuma longa* methanol extract (Extract-8). Similarly, the composition-6 and composition-8 derived from *T. indica* seed mixed extract (Extract-5) also showed synergistic activity with TNFα inhibitions of 91.14% and 86.69% respectively, when compared to those shown by their individual ingredients Extract-5 (34.27%) and Extract-8 (78.78%). The other compositions also showed improved TNFα inhibition as summarized in Table 4. The compositions of the current invention were further tested to evaluate their efficacy to inhibit MMP-3 in human SW982 synovial cells. The compositions-1, -2 and -4 derived from *Tamarindus indica* seed methanol extract (Extract-1) and composition-6 and composition-8 derived from the *T. indica* seed mixed extract (Extract-5) also showed complete inhibition of MMP-3 with 102.1%, 99.2% 95.07%, 106.38% and 115.27% reductions respectively in MMP-3 production at 25 μg/ml concentration. Their individual ingredients Extract-1, Extract-5 and Extract-8 in comparison showed 26.02%, 39.6% and 82.81% inhibition of MMP-3 respectively. The improved efficacy shown by the compositions of the present invention in vitro was further confirmed in vivo using in Adjuvant Induced model of arthritis. The Composition-6 containing *Curcuma longa* extract (Extract-8) and *T. indica* extract (Extract-5) showed better efficacy in Adjuvant induced model of arthritis compared to its individual components, Extract-5 and Extract-8 as summarized in Table 6. Finally, composition-11 containing *T. indica* seed mixed extract and *Curcuma longa* extract along with excipients showed dose dependent inhibition of paw edema with 22.3% and 30.3% reductions of paw edema at doses 200 mg and 40 mg/kg body weight respectively as depicted in FIGS. 2A and 2B. Percentage weight bearing capacity was measured in all the groups before induction and on $20^{th}$ day of treatment using Incapacitance Meter (IITC Life Science Inc., CA) and the data is summarized in Table-7 and FIG. 2C. The composition-11 showed dose dependent improvement of weight bearing and 400 mg/kg treated group showed statistically significant improvement in weight bearing compared to disease control group.

From the foregoing it is obvious that the mixed extracts of *T. indica* seed comprising proanthocyanidins containing alcohol extracts and polysaccharide containing water extracts; and the compositions comprising proanthocyanidin containing *tamarindus* seed extracts and *Curcuma longa* extracts provides improved treatments for inflammation, arthritis, joint pain, rheumatoid arthritis, osteoarthritis, chronic non-rheumatoid arthritis, collagen degradation.

In the primary embodiment, the invention relates to synergistic compositions comprising *T. indica* seed extract in combination with at least one extract derived from the plant materials selected from *Curcuma longa, Zingiber officinale, Annona squamosa, Andrographis paniculata, Withania somnifera*, preferably, the extract of *Curcuma longa*. In the other primary embodiment, the invention provides an improved extract of *Tamarindus indica* seed obtained by combining the organic solvent extract containing proanthocyanidins and water extract of *Tamarindus indica* seeds containing polysaccharides at selected ratios.

Thus the present invention discloses a novel synergistic composition which comprises a combination of therapeutically effective amounts of:
a) an alcoholic/hydroalcoholic extract of *Tamarindus indica* seed comprising proanthocyanidins either alone or in combination with water extract of *Tamarindus indica* seed comprising polysaccharides,
b) *Curcuma longa* rhizome extracts comprising curcuminoids,
c) optionally containing pharmaceutically or nutraceutically or dietetically acceptable carriers/excipients useful for the prevention or treatment of atleast one condition selected from inflammation, arthritis, joint pain, rheumatoid arthritis, osteoarthritis, chronic non-rheumatoid arthritis, collagen degradation.

The present synergistic composition for the treatment of osteoarthritis comprising *Tamarindus indica* seed and *Curcuma longa* rhizome extracts may also be formulated as a dietary supplement.

In other embodiment, the ratio between *Tamarindus indica* extract to the extract of *Curcuma longa* rhizome vary in the range from 1:10 to 10:1.

In a preferred embodiment, the present invention provides a synergistic dietary supplement/herbal composition consisting of *Tamarindus indica* extract or its fraction in the range from 10% to 80% by weight, *Curcuma longa* extract or fraction in the range from 20% to 80% by weight and (c) optionally containing excipients/carriers varying in the range of 0-30%.

In another preferred embodiment, the synergistic composition(s) comprises (a) *Tamarindus indica* seed extract varies in the range from 40% to 70%, (b) *Curcuma longa* rhizome extract varies in the range of 20% to 40%; and (c) optionally containing excipients/carriers varying in the range of 0-15%.

In yet another preferred embodiment, the synergistic composition(s) comprises a) 60% of *Tamarindus indica* seed extract b) 30% of *Curcuma longa* rhizome extract and c) 10% of excipients/carriers.

According to other primary embodiment, the invention provides a novel synergistic *Tamarindus indica* seed extract comprising a) 1% to 99% by weight of alcohol or hydroalcohol extract primarily consisting of proanthocyanidins and b) 1 to 50% by weight of water extract consisting of predominantly polysaccharides, optionally containing pharmaceutically or nutraceutically or dietetically acceptable carriers/excipients useful for the treatment of at least one disease condition selected from inflammation, arthritis, Joint pain, rheumatoid arthritis and osteoarthritis.

In another embodiment, the solvents that can be used for preparing the extracts or fractions of the herbs, seed of *T. indica* and rhizome of for *C. longa* can be selected from ethylacetate, acetone, acetic acid, C1-C5 alcohols such as ethanol, methanol; water and mixtures thereof. Specifically, the alcohol that can be used for preparing *Tamarindus indica* seed extract comprising proanthocyanidin compounds may be selected from the group consisting of methanol, ethanol, propanol, isopropanol, butanol and tert-butanol and mixtures thereof. The *Curcuma longa* extract may be prepared from *Curcuma longa* rhizome using solvents selected from methanol, ethanol, propanol, isopropanol, n-butanol, tert-butanol, acetone, ethyl acetate and the fractions enriched in total curcuminoids derived from the said extracts.

The term "carriers/excipients" or "pharmaceutically acceptable carriers," as used herein, refers to the diluents, excipients, acceptable agents or the like that are well known by those of ordinary skill in the art and can be used in the preparation of pharmaceutical composition.

The synergistic composition is formulated with pharmaceutically or nutraceutically or dietetically acceptable excipients, carriers, or diluents into lozenge, tablet, film coated tablet, capsule, soft capsule, granule, powder, pill, solution, emulsion, injection solution, injection, ointment, cream, spray, inhalant, soft gel, liquid, lotion, implant, or transdermal patch for various administration routes. The pharmaceutically or nutraceutically or dietetically acceptable carriers/excipients that can be used for the preparation of the compositions may be selected from surfactants, binders, diluents, disintegrants, lubricants, preservatives, stabilizers, buffers, polymers, colors, flavors, suspensions and drug delivery systems.

The present invention further provides compositions comprising *Tamarindus indica* seed extract and *Curcuma longa* rhizome extract as described herein, optionally containing a pharmaceutically acceptable carrier for the prevention, control and treatment of one or more components of arthritis or rheumatoid arthritis. Non limiting examples of arthritis include rheumatoid (such as soft-tissue rheumatism and non-articular rheumatism, fibromyalgia, fibrositis, muscular rheumatism, myofascial pain, humeral epicondylitis, frozen shoulder, Tietze's syndrome, fascitis, tendinitis, tenosynovitis, bursitis), juvenile chronic, joint disorders, spondyloarthropathies (ankylosing spondylitis), osteoarthritis, hyperuricemia and arthritis associated with acute gout, chronic gout and systemic lupus erythematosus and degenerative arthritis.

In yet another embodiment, the invention also provide the methods of treating inflammation and disease conditions related to inflammation, which include but not limited to inflammation, arthritis, joint pain, rheumatoid arthritis, osteoarthritis, chronic non-rheumatoid arthritis, collagen degradation in subjects or mammals in need thereof by administering improved extracts derived from *Tamarindus indica* or compositions comprising *Tamarindus indica* seed extract and *Curcuma longa* rhizome extract, optionally containing excipients/diluents.

Accordingly, the invention provides a method for treating a disease condition selected from inflammation, arthritis, joint pain, rheumatoid arthritis, osteoarthritis, chronic non-rheumatoid arthritis, collagen degradation in a patient in need thereof comprising administering to the patient an effective amount of novel synergistic composition(s) comprising a) an alcoholic/hydroalcoholic extract of *Tamarindus indica* seed comprising proanthocyanidins either alone or in combination with water extract of *Tamarindus indica* seed comprising polysaccharides; b) *Curcuma longa* rhizome extract comprising curcuminoids, optionally containing pharmaceutically or nutraceutically or dietetically acceptable carriers/excipients.

In an alternate embodiment, the invention provides a method for treating a disease condition selected from inflammation, arthritis, joint pain, rheumatoid arthritis, osteoarthritis, chronic non-rheumatoid arthritis, collagen degradation in a patient in need thereof comprising administering to the patient an effective amount of novel synergistic *Tamarindus indica* seed extract comprising a) 1% to 99% by weight of alcohol or hydroalcohol extract primarily consisting of proanthocyanidins and b) 1 to 50% by weight of water extract consisting of predominantly polysaccharides, optionally containing pharmaceutically or nutraceutically or dietetically acceptable carriers/excipients In yet another embodiment, the invention provides use of a novel synergistic composition comprising a combination of therapeutically effective amount of; a) *Tamarindus indica* seed extract selected from alcohol or hydroalcohol extract comprising proanthocyanidins either alone or in combination with *Tamarindus indica* seed water extract containing polysaccharides, b) *Curcuma longa* rhizome extract comprising curcuminoids, c) optionally containing pharmaceutically or Nutraceutically or dietetically acceptable carriers/excipients for the prevention or treatment of at least one condition selected from inflammation, arthritis, joint pain, rheumatoid arthritis, osteoarthritis, chronic non-rheumatoid arthritis, collagen degradation.

In a further embodiment, the invention provides use of a novel *Tamarindus indica* seed extract comprising a) 1% to 99% by weight of seed alcohol or hydroalcohol extract comprising proanthocyanidins and b) 1 to 50% by weight of water extract containing predominantly polysaccharides, optionally containing pharmaceutically or nutraceutically or dietetically acceptable carriers/excipients useful for the treatment of at least one disease condition selected from inflammation, arthritis, Joint pain, rheumatoid arthritis and osteoarthritis.

The most suitable route and dosage for treatment will be easily determined by those skilled in the art. Dosage will depend on the nature and state of the symptoms being treated, age and general physical conditions of the patient being treated, administration route and any therapies practiced previously.

The synergistic composition of the present invention can also be delivered orally, the dosage form of which can be solid or liquid. Solid compositions include tablets, pills, capsules, powders, granules and the like. Oral dosage forms also include gargles and lozenges. Capsules include hard and soft capsules. Such oral solid compositions can be used alone or in combination with diluents, chelating agents, disintegrating agents, lubricants, stabilizers, and co solvents, to form the required dosage forms by using known methods in the art.

Preferred examples of solid carriers or diluents or excipients include but not limited to glucose, fructose, sucrose, maltose, yellow dextrin, white dextrin, aerosol, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, calcium salts, pigments, flavors and preservatives.

Preferred examples of liquid carriers (diluents) include, distilled water, saline, aqueous glucose solution, alcohol (e.g. ethanol), propylene glycol and polyethylene glycol; and oily carriers such as various animal and vegetable oils, white soft paraffin, paraffin and wax.

Another embodiment of the invention provides that the quantity of the present inventive compositions in the above-mentioned various formulations, dietary supplements, food and beverage compositions may also not be uniform and varies depending on the nature of the formulation and suggested human or animal dosage of the compositions, for example, about 0.001% to 99%, more preferably about 0.001 to 90 wt % of the dosage of the composition.

The specific examples below are to be construed as merely illustrative, and not limitative of the remainder of the disclosure in any way whatsoever. Without further elaboration, it is believed that one skilled in the art can, based on the description herein, utilize the present invention to its fullest extent.

EXPERIMENTAL

EXAMPLE—1

Preparation of *Tamarindus indica* Alcohol Extracts

Dried seed of the plant material (1.0 Kg) was pulverized to coarse powder, extracted with alcohol (Methanol, 8 L) at 60-65° C. for 2 hrs. Extraction process repeated thrice using alcohol in the ratio of 1:5-1:7 W/V with respect to the plant material. All the extracts were combined, the combined alcohol extracts were fine filtered, and the clear extract was evaporated under at 50-55° C. under vacuum to give thick paste. The above material dried under high vacuum for 8-10 hrs to give alcohol extract as dry powder (Extract-1, 130 g).

The seed left over residue was then extracted with water (8 L). The extraction was repeated twice with water (6 L). The water extracts were combined and fine filtered. The extract was evaporated under vacuum and the residue was subjected to final drying in vacuum dryer at 75 to 85° C. to obtain water extract (Extract-2, 30 g). These two extracts (Extract-1 and Extract-2) were combined in 1:1, sieved and blended to obtain homogenous powder (Extract-3).

Ethanol extract of *Tamarindus indica* seeds and water of seed residue were prepared using the process described above to obtain 119.2 g of ethanol extract (Extract-1A) and 36.4 g of water Extract (Extract-2A) respectively. The chemical profile of the extracts from the ethanol process matched exactly with those obtained from the methanol process. Other solvents such as acetone, propanol, isopropanol, n-butanol and tert-butanol can also be used for preparing the extracts with more or less similar chemical profile.

The physical and chemical parameters of extract-1 are evaluated using the standard procedure. The proanthocyanidin (PAC) content was evaluated using the UV Spectrophotometric method (USP 29-NF 24 page 2552) and the polysaccharide content was evaluated using the gravimetric method as per the following test procedures.

Procedure for the Estimation of Polysaccharides:

Weighed about 2.5 gm of sample into a 250 ml beaker, added 15 ml of water, covered the beaker with a watch glass and heated the solution on a water bath to dissolve the solids. The solution was cooled, centrifuged to collect the clear liquid in a 250 ml beaker and added 25 ml of 80% methanol, mixed well and then added 50 ml of 95% methanol and stirred on a magnetic stirrer for one hour. The precipitate was filtered quantitatively through a previously dried and weighed What man No. 1 filter paper, washed the beaker and filter paper with 2×25 ml of 80% methanol. Dried the residue at 105° C.±2° C. for one hour in an oven, cooled and weighed the precipitate. Calculated the percentage of polysaccharides using the formula, Percentage of polysaccharides=weight of the residue/weight of the sample X 100. Polysaccharide content in extract-1 is 0%.

Procedure for the Estimation of Proanthocyanidins (procyanidins):

1.0 ml each of the standard and sample solutions (Concentration of 95 µg/ml Procyanidins) and methanol were transferred into three separate 10 ml vials. To each of the vials added 6.0 ml of reagent A. (A mixture of butanol and hydrochloric acid in a ratio of 95:5) and 0.25 ml of reagent solution B. (A mixture of 2% ferric ammonium sulphate and 17.5 ml Hydrochloric acid). Mixed and heated the vials in a water bath for 40 min, quickly cooled to room temperature and diluted with reagent A to volume 10 ml. Determined the absorbance of the solution obtained from the standard solution and the sample solution, using the methanol containing solution as a blank. The percentage of the total procyanidins in the extract was calculated using the following formula.

Total procyanidins=Absorbance of the sample/absorbance of the standard X concentration of the standard/concentration of the sample X purity of the standard. (Reference: USP 37 NF32 Pages 5484). The proanthocyanidin content in extract −1 is >90%.

The properties of methanol extract are summarized in table 1. The extract was subjected to intensive purification using Flash column chromatography and preparative HPLC purification to yield several flavanoids and proanthocyanidin compounds. The structures of selected flavanols and proanthocyanidin compounds were characterized using NMR and LC-MS/MS analysis on Xevo G2 QTOF mass spectrometer and the structures are summarized in FIG. 1. The mass spectrometric analysis showed the presence of catechin, epicatechin, procyanidin dimer, procyanidin trimer, procyanidin tetramer, procyanidin pentamer and procyanidin hexamer in the alcoholic extracts of *Tamarindus* seed.

EXAMPLE—2

Preparation of *Tamarindus indica* WaterExtract

Dried seed of the plant material (1.0 Kg) was pulverized to coarse powder, extracted with water (8 L) for at 85-95° C. for 2 h. The extraction was repeated twice with water (6 L). The water extracts were combined and fine filtered. The extract was evaporated under vacuum and the residue was subjected to final drying in vacuum dryer at 75 to 85° C. to obtain direct water extract (Extract-4, 90 g). The proanthocyanidin and polysaccharide contents in extract-4 were determine using the above procedures. The proanthocyanidin content: 0.36%. Polysaccharide content: 24.49%.

EXAMPLE—3

Preparation of *Tamarindus indica* mixed Extracts

*Tamarindus indica* mixed extract (Extract-3). *Tamarindus indica* seed methanol extract (Extract-1, 1 g) was combined with *Tamarindus indica* seed residue water extract (Extract-2, 1 g) and the mixture blended uniformly to obtain Extract-3.

*Tamarindus indica* mixed extract (Extract-5). *Tamarindus indica* seed methanol extract (Extract-1, 10 g) was combined with *Tamarindus indica* seed residue water extract (Extract-2, 1 g) and the mixture blended uniformly to obtain Extract-5.

*Tamarindus indica* mixed extract (Extract-6). *Tamarindus indica* seed methanol extract (Extract-1, 10 g) was combined with *Tamarindus indica* seed water extract (Extract-4, 1 g) and the mixture blended uniformly to obtain Extract-6.

*Tamarindus indica* mixed extract (Extract-7). *Tamarindus indica* seed methanol extract (extract-1, 10 g) was combined with *Tamarindus indica* seed residue water extract (Extract-2, 2 g) and the mixture blended uniformly to obtain Extract-7.

Compositions with varying ratios of above ingredients can be prepared using the same process.

EXAMPLE—4

Preparation of *Curcuma longa* Alcohol Extract

Dried rhizomes of the plant material (1.0 Kg) was pulverized to coarse powder, extracted with methanol (9 L) for at 60-65° C. for 2 hrs. Extraction process repeated thrice using methanol in the ratio 1:6 W/V with respect to the plant material. All the extracts were combined, the combined alcohol extracts were fine filtered, and the clear extract was evaporated under at 50-55° C. under vacuum to give a loosepaste. The above material dried under high vacuum for 6-8 h to give a thick paste (95 g; Extract-8, 20.1% total curcuminoids).

The acetone, ethanol, ethylacetate and methylisobutylketone (MIBK) extracts of *Curcuma longa* rhizomes were prepared using the same experimental procedure to obtain acetone extract (72 g, 30% total curcuminoids), ethanol extract (80 g, 24% total curcuminoids), ethylacetate extract (64 g, 29.7% total curcuminoids) and MIBK extract (89 g, 22% total curcuminoids respectively.

The above extracts were subjected to acetone wash to obtain extracts enriched up to 60% total curcuminoids. Repeated crystallization in IPA/methanol yielded enriched extracts containing >95% total curcuminoids.

EXAMPLE—5

Composition-1: The composition-1 was prepared by combining the alcohol extract of *Tamarindus indica* (Extract-1) and alcohol extract of *Curcuma longa* (Extract-8) in the ratio of 1:1.

EXAMPLE—6

Composition-2: The composition-2 was prepared by combining the methanol extract of *Tamarindus indica* (Extract-1) and methanol extract of *Curcuma longa* (Extract-8) in the ratio of 2:1.

EXAMPLE—7

Composition-3: The composition-3 was prepared by combining the alcohol extract of *Tamarindus indica* (Extract-1) and alcohol extract of *Curcuma longa* (Extract-8) in the ratio of 3:1.

EXAMPLE—8

Composition-4: The composition-4 was prepared by combining the methanol extract of *Tamarindus indica* (Extract-1) and methanol extract of *Curcuma longa* (Extract-8) in the ratio of 1:3.

EXAMPLE—9

Composition-5: The composition-5 was prepared by combining the Extract-5 of *Tamarindus indica* and alcohol extract of *Curcuma longa* (Extract-8) in the ratio of 3:1.

EXAMPLE—10

Composition-6: The composition-6 was prepared by combining the Extract-5 of *Tamarindus indica* and methanol extract of *Curcuma longa* (Extract-8) in the ratio of 2:1.

EXAMPLE—11

Composition-7: The composition-7 was prepared by combining the extract-6 of *Tamarindus indica* and alcohol extract of *Curcuma longa* (Extract-8) in the ratio of 3:1.

EXAMPLE—12

Composition-8: The composition-8 was prepared by combining Extract-5 of *Tamarindus indica* seed and methanol extract of *Curcuma longa* (Extract-8) in the ratio of 1:2.

EXAMPLE—13

Composition-9: The composition-1 was prepared by combining Extract-7 of *Tamarindus indica* seed and alcohol extract of *Curcuma longa* (Extract-8) in the ratio of 3:1.

EXAMPLE—14

Composition-10: The composition-1 was prepared by combining Extract-7 of *Tamarindus indica* seed and methanol extract of *Curcuma longa* (Extract-8) in the ratio of 1:3.

EXAMPLE—15

Composition-11: The composition-11 was prepared by combining 60 parts of *Tamarindus indica* seed extract [54 parts of *Tamarindus indica* seed methanol extract (Extract-1)+6 parts of *Tamarindus indica* seed residue water extract (Extract-2)], 30 parts of methanol extract of *Curcuma longa* (Extract-8), 8 parts of microcrystalline cellulose and 2 parts of silica (Syloid 244FP).

EXAMPLE—16

5-Lipoxygenase Enzyme (5-LOX) Inhibitory Activity
Synergistic Anti-Inflammatory Activity of the Compositions-1 to -9 Containing the Extracts of *T. indica* Seed Extracts Extract-1 to Extract 7 and *Curcuma longa* Rhizome (Extract-8).

5-Lipoxygenase enzyme inhibitory activity was measured using the method of Lip Yong Chung et al., (Pharmaceutical Biology, Vol. 47 (12), 1142-1148, and 2009). The assay mixture contained 80 µM linoleic acid and sufficient amount of potato 5-lipoxygenase in 50 mM Tris HCl buffer (pH 7.4). 5 µL of 5-LOX enzyme was added to 175 µL of 50 mM Tris HCl buffer. The reaction was initiated by the addition of 5 µL linoleic acid (final conc. 140 µM) in 50 mM Tris HCl buffer followed by incubation at 25° C. in dark 20 min. The total volume of the reaction mixture is 185 µL. The assay was terminated by the addition of 65 µL freshly prepared fox reagent. After incubation for 20 min the absorbance was read using Xmark Micro plate spectrophotometer (BIO-RAD) at 595 nm. The reaction was monitored for 120 sec and the inhibitory potential of the test substances extracts and compositions was measured by incubating various concentrations of test substances two minutes before the addition of linoleic acid. All assays were performed three times. Percentage inhibition was calculated by comparing slope of the curve obtained for test substances with that of the control.

The percentage inhibitions (IC$_{50}$ values) of the compositions-1 to -9 and the extracts of *T. indica* seed (Extract-1 to Extract-7) and *Curcuma longa* rhizome (Extract-8) are summarized in Table-3.

TABLE 3

5-Lipoxygenase enzyme (5-LOX) inhibitory activity

| S. No | Description | 5-LOX (IC50-µg/ml) |
|---|---|---|
| 1 | Extract-1 | 15.62 |
| 2 | Extract-1A | 13.07 |
| 3 | Extract-2 | >100 |
| 4 | Extract-3 | 12.02 |
| 5 | Extract-4 | >100 |
| 6 | Extract-5 | 13.05 |
| 7 | Extract-6 | 10.72 |
| 8 | Extract-7 | 11.08 |
| 9 | Extract-8 | 17.96 |
| 10 | Composition-1 | 8.98 |
| 11 | Composition-2 | 7.81 |
| 12 | Composition-3 | 9.56 |
| 13 | Composition-4 | 9.57 |
| 14 | Composition-5 | 9.57 |
| 15 | Composition-6 | 9.46 |
| 16 | Composition-7 | 12.67 |

The above 5-lipoxygenase inhibitory activity values in the Table-3 clearly shows the synergistic efficacy of the composition comprising *Tamarindus indica* extract and *Curcuma longa* extract in inhibiting the 5-lipoxygenase enzyme. The results of this experiment showed that composition of the extracts showed greater 5-lipoxygenase inhibitory activity than the individual extracts.

EXAMPLE—17

Inhibition of Tumor necrosis factor-α (TNF-α) in vitro by *Tamarindus indica* extracts (Extracts-1 to -7) and the compositions (Compositions-1 to -10) containing *Tamarindus indica* extracts and *Curcuma longa* extracts.

The anti-inflammatory activities of extracts and compositions were assessed in a cell based in vitro assay. Briefly, THP-1 human monocytes cells were washed and re-suspended in phenol red free Dulbecco's Modified Eagle's Medium (DMEM) supplemented with 1% fetal Bovine serum (FBS). Equal number of cells was added to each well of a 96-well TC plate and the cells were pretreated for 2 h with various concentrations of test substances (ranging from 0.5 to 50 µg/ml; solutions prepared in culture medium from a stock solution containing 50 mg/1 mL DMSO of each test compound) of extracts and compositions. The inflammatory response was induced by treatment with 100 ng/ml of LPS for 4 h at 37° C. in presence of 5% CO$_2$. The vehicle control culture wells received 0.1% DMSO in culture medium. The cell culture supernatants were collected and assessed for secretary pro-inflammatory cytokine, TNFα. The TNF-α concentration was quantitatively measured by highly specific and sensitive Enzyme Immuno Assay (EIA) kit supplied by R&D Systems, USA. The enzyme immuno assay was performed based on the protocol provided by the vendor. The inhibitory concentration for 50% inhibition (IC$_{50}$) of TNF-α was determined from a plot drawn for ingredient concentration against TNF-α level. Table-4 shows a comparison of concentrations of extracts and compositions for 50% inhibition of TNF-α(IC$_{50}$) in cell based in vitro model.

TABLE 4

TNF-α Inhibition

| S. No | Description | % inhibition at 10 µg/ml |
|---|---|---|
| 1 | Extract-1 | 48.13 |
| 2 | Extract-1A | 63.37 |
| 3 | Extract-2 | 2.78 |
| 4 | Extract-4 | 18.90 |
| 5 | Extract-5 | 34.27 |
| 6 | Extract-6 | 42.94 |
| 7 | Extract-8 | 78.78 |
| 8 | Composition-1 | 99.20 |
| 9 | Composition-2 | 81.94 |
| 10 | Composition-3 | 65.09 |
| 11 | Composition-4 | 95.25 |
| 12 | Composition-5 | 52.61 |
| 13 | Composition-6 | 91.14 |
| 14 | Composition-8 | 86.69 |
| 15 | Composition-9 | 73.04 |
| 16 | Composition-10 | 91.54 |

EXAMPLE—18

Inhibition of Matrix Metalloproteinase-3 (MMP-3) Activity

MMP-3 was evaluated in IL-β induced SW982 human synovial cells. Briefly, the SW982 cells were cultured in DMEM with 2 mM Glutamine, 100 U/mL penicillin, 100 mg/mL streptomycin and 10% fetal bovine serum (Hyclone, Logan, Utah). Five thousand cells per well were seeded into a 96-well cell culture plate (Corning, USA) one day before the experiment. The culture media was replaced with fresh DMEM containing 1% fetal bovine serum. Extracts and Compositions were serially diluted in medium, ranging from 2.5 µg to 100 µg/ml and were pre-incubated with cells for 2 hour at 5% CO$_2$ at 37° C., and then stimulated with 10 ng/ml human recombinant IL-1β(R&D System, Minneapolis, Minn.) for 24 hours. The culture supernatant was harvested and used to measure MMP-3 production by ELISA development kit (R&D System, Minneapolis, Minn., USA). The MMP-3 concentration in cell free culture supernatant was estimated quantitatively by interpolating the optical densities into the standard curve generated from known concentrations of MMP-3. The percentage inhibition data is summarized in (Table -5).

TABLE 5

MMP-3 inhibition

| S. No | Description | % Inhibition at 25 µg/ml |
|---|---|---|
| 1 | Extract-1 | 26.02 |
| 2 | Extract-1A | 36.60 |
| 3 | Extract-2 | −12.1 |
| 4 | Extract-3 | 46.71 |
| 5 | Extract-4 | −13.15 |
| 6 | Extract-5 | 39.58 |
| 7 | Extract-6 | 46.52 |
| 8 | Extract-7 | 36.60 |
| 9 | Extract-8 | 82.81 |
| 10 | Composition-1 | 102.07 |
| 11 | Composition-2 | 99.20 |
| 12 | Composition-3 | 84.75 |
| 13 | Composition-4 | 95.07 |
| 14 | Composition-5 | 89.86 |
| 15 | Composition-6 | 106.38 |
| 16 | Composition-8 | 115.27 |

TABLE 5-continued

MMP-3 inhibition

| S. No | Description | % Inhibition at 25 µg/ml |
|---|---|---|
| 17 | Composition-9 | 55.62 |
| 18 | Composition-10 | 95.07 |

EXAMPLE—19

Efficacy of *T. indica* Extract (Extract-5) and its Synergistic Composition-6 Aainst Adjuvant Induced Arthritis in Sprague Dawley Rats.

Sprague Dawley Rats were housed in solid bottom autoclaved polypropylene cages at three rats per cage with stainless steel top grill. Animals were provided with rodent pellet feed and mineral water ad libitum. The animals were acclimatized for a period of 3 days prior to enrollment into the experiment and they are habituated/adapted to the experimenter and to the experimental conditions for measurement of hind limb weight bearing capacity in the Incapacitance meter. A group of 42 animals were examined and 36 healthy SD rats were selected for the study and were randomly assigned to one of six different groups based on the paw volume, i. e., normal control, vehicle control, three groups supplemented with test substances[*Tamarindus indica* extract (Extract-5; 400 mg), *Curcuma longa* extract (Extract-8; 400 mg) and composition-6 (400 mg) containing *Tamarindus indica* extract (Extract-5) and *Curcuma longa* extract (Extract-8)]. 7 days after administration of test item, reference item or vehicle, on day 8 arthritis was induced in rats of all groups except G1 by a single subcutaneous injection of 0.1 mL suspension of heat killed *M. tuberculosis* (300 µg/animal) in Incomplete Freund's Adjuvant (Sigma-Aldrich, USA), into the sub plantar region of left hind limb. Control group animals were injected with 0.1 mL normal saline (0.9% w/v sodium chloride). The vehicle, test items and reference drug were administered till completion of the study i.e. 35 days. Paw volume was measured by a Plethysmometer (Pan Lab, LE7500) on day 0 (prior to treatment) and day 35. The difference between the final and initial paw volume was considered as edema volume. The in vivo anti-inflammatory responses of test compounds were estimated by calculating the percentage inhibition of paw edema when compared to the paw edema observed in the CMC supplemented control group. The data is summarized in Table-6. The composition-6 showed better inhibition of paw edema compared to the individual ingredients, Extract-5 and Extract-8.

TABLE 6

| S. No | Test compound | % inhibition of Paw edema |
|---|---|---|
| 1 | *C. longa* extract (Extract-8) | 7.11 |
| 2 | *T. indica* extract (Extract-5) | 7.11 |
| 3 | Compoisition-6 | 16.44 |

EXAMPLE—20

Anti-Inflammatory Activity of Composition-11 in Adjuvant Induced Arthritis in Sprague Dawley Rats.

Sprague Dawley Rats were housed in solid bottom autoclaved polypropylene cages at three rats per cage with stainless steel top grill. Animals were provided with rodent pellet feed and mineral water ad libitum. The animals were acclimatized for a period of 3 days prior to enrollment into the experiment and they are habituated/adapted to the experimenter and to the experimental conditions for measurement of hind limb weight bearing capacity in the Incapacitance meter. A group of 35 animals were examined and 30 healthy SD rats were selected for the study and were randomly assigned to one of five different groups based on the paw volume, i. e., normal control (G1), vehicle control (G2), two groups (G3 & G4) supplemented with test substances composition-11 (200 mg 400 mg) and with reference drug prednisolone 10 mg/kg (G5). After 7 days administration of test item, reference item or vehicle, on day 8 arthritis was induced in rats of all groups except G1 by a single subcutaneous injection of 50 µL Complete Freund's Adjuvant (Sigma-Aldrich, USA), into the sub plantar region of left hind limb. Control group animals were injected with 0.1 mL normal saline (0.9% w/v sodium chloride). The vehicle, test items and reference drug were administered till completion of the study i.e. 20 days. Paw volume was measured by a Plethysmometer (Pan Lab, LE7500) on day 0 (prior to treatment) and day 20. The difference between the final and initial paw volume was considered as edema volume. The in vivo anti-inflammatory responses of test compounds were estimated by calculating the percentage inhibition of paw edema when compared to the paw edema observed in the CMC supplemented control group. The composition-11 showed statistically significant and dose dependent inhibition of paw edema compared to disease control group (G2) as summarized in FIGS. 2A and 2B. The treatment groups supplemented with 200 mg and 400 mg of composition-11 showed 22.3% and 30.3% inhibition of paw edema, the prednisolone in comparison showed 69.7% inhibition. Percentage weight bearing capacity was measured in all the groups before induction and on $20^{th}$ day of treatment using Incapacitance Meter (IITC Life Science Inc., CA). The data was summarized in Table-7 and FIG. 2C. The composition-11 showed dose dependent improvement of weight bearing and 400 mg/kg treated group showed statistically significant improvement in weight bearing compared to disease control group (G2).

TABLE 7

Effect of Composition 11 on mean left hind limb weight bearing capacity (g) in AIA
Percent Weight Bearing on Left Hind Limb

| Group | Before Induction | Day-20 |
|---|---|---|
| G1-Normal control + Vehicle | 48.67 ± 0.42 | 49.02 ± 0.48 |
| G2-AIA + Vehicle | 50.29 ± 0.53 | 30.54 ± 1.80## |
| G3-AIA + Composition-11 (200 mpk) | 49.80 ± 0.56 | 33.21 ± 2.82 |
| G4-AIA + Composition-11 (400 mpk) | 49.53 ± 0.55 | 37.57 ± 1.63* |
| G5-AIA + Prednisolone (10 mpk) | 49.57 ± 0.55 | 49.88 ± 1.13** |

Data are expressed as mean ± S.E.M of six rats per group.
$p < 0.01$ vs normal control (G1);
*$p < 0.05$;
**$p < 0.01$ vs AIA control (G2) by One-way ANOVA followed by Dunnett's Test.

We claim:

1. A dosage form comprising:
a combination of therapeutically effective amounts of:
a) A *Tamarindus indica* seed extract comprising:
an alcohol or hydroalcohol extract of a *Tamarindus indica* seed, wherein the alcohol or hydroalcohol extract comprises proanthocyanidins; and
a water extract of a *Tamarindus indica* seed, the water extract comprising polysaccharides;
wherein the alcohol or hydroalcohol extract of the *Tamarindus indica* seed and the water extract of the *Tamarindus indica* seed are used in a ratio ranging from 1:1 to 10:1; and
b) A *Curcuma longa* rhizome extract comprising curcuminoids,
wherein the *Tamarindus indica* seed extract and the *Curcuma longa* rhizome extract are used in a ratio ranging from 1:3 to 3:1; and
a pharmaceutically, nutraceutically, or dietetically acceptable excipient or carrier.

2. A composition comprising a combination of:
a) a *Tamarindus indica* seed extract comprising:
an alcohol or hydroalcohol extract of a *Tamarindus indica* seed, the alcohol or hydroalcohol extract comprising proanthocyanidins; and
a water extract of a *Tamarindus indica* seed, the water extract comprising polysaccharides; and
b) a *Curcuma longa* rhizome extract comprising curcuminoids, wherein:
the combination is present in an amount which is effective for the treatment of inflammation,
the *Tamarindus indica* seed extract and the *Curcuma longa* rhizome extract are used in a ratio ranging from 1:3 to 3:1, and
the *Tamarindus indica* seed extract comprises:
from 50% to 91% by weight of an alcohol or hydroalcohol extract of a *Tamarindus indica* seed, the alcohol or hydroalcohol extract comprising proanthocyanidins; and
from 9% to 50% of a water extract of a *Tamarindus indica* seed, the water extract comprising predominantly polysaccharides.

3. The composition according to claim 2, wherein the alcohol used for preparing the alcohol or hydroalcohol extract of the *Tamarindus indica* seed is selected from the group consisting of methanol, ethanol, propanol, isopropanol, butanol, tert-butanol, and mixtures thereof.

4. The composition according to claim 2, wherein the *Curcuma longa* rhizome extract is prepared from a *Curcuma longa* rhizome using a solvent selected from the group consisting of methanol, ethanol, propanol, isopropanol, n-butanol, tert-butanol, acetone, ethyl acetate, and mixtures thereof.

5. The composition according to claim 2, further comprising a pharmaceutically, nutraceutically, or dietetically acceptable carrier or excipient.

6. The composition according to claim 5, wherein the pharmaceutically, nutraceutically, or dietetically acceptable carrier or excipient is selected from the group consisting of surfactants, binders, diluents, disintegrants, lubricants, preservatives, stabilizers, buffers, polymers, colors, flavors, suspensions and drug delivery systems.

7. The dosage form according to claim 1, wherein the combination comprises from greater than 0% to 30% of the excipient or carrier.

8. The dosage form according to claim 1, wherein the combination comprises:
from 40% to 70% of the *Tamarindus indica* seed extract; and
from greater than 0% to 15% of the excipient or carrier.

9. The dosage form according to claim 1, wherein the combination comprises:
a) 60% of the *Tamarindus indica* seed extract;
b) 30% of the *Curcuma longa* rhizome extract comprising curcuminoids; and
c) 10% the excipient or carrier.

10. The composition according to claim 2, wherein the composition is formulated to be administered orally or topically.

11. A method for treating at least one disease condition selected from the group consisting of inflammation, arthritis, joint pain, rheumatoid arthritis, osteoarthritis, chronic non-rheumatoid arthritis, and collagen degradation in a patient in need thereof, comprising administering to the patient an effective amount of the composition as claimed in claim 2.

12. A method for treating at least one disease condition selected from the group consisting of inflammation, arthritis, joint pain, rheumatoid arthritis, osteoarthritis, chronic non-rheumatoid arthritis, and collagen degradation in a patient in need thereof, comprising administering to the patient an effective amount of the dosage form according to claim 9.

13. The composition according to claim 2, wherein the composition is useful for the prevention or treatment of at least one condition selected from inflammation, arthritis, joint pain, rheumatoid arthritis, osteoarthritis, chronic non-rheumatoid arthritis, collagen degradation.

14. A method for treating at least one disease condition selected from the group consisting of inflammation, arthritis, joint pain, rheumatoid arthritis, osteoarthritis, chronic non-rheumatoid arthritis, and collagen degradation in a patient in need thereof, comprising administering to the patient an effective amount of the dosage form as claimed in claim 7.

* * * * *